United States Patent [19]

Okamoto et al.

[11] Patent Number: 4,677,473
[45] Date of Patent: Jun. 30, 1987

[54] SOLDERING INSPECTION SYSTEM AND METHOD THEREFOR

[75] Inventors: Shinji Okamoto; Kazunari Yoshimura, both of Yawata; Tomoharu Nakahara, Nishinomiya, all of Japan

[73] Assignee: Matsushita Electric Works, Ltd., Osaka, Japan

[21] Appl. No.: 795,912

[22] Filed: Nov. 7, 1985

[30] Foreign Application Priority Data

Jun. 21, 1985 [JP] Japan ................ 60-135418

[51] Int. Cl.4 .................. H04N 7/18; F21V 33/00
[52] U.S. Cl. ........................ 358/101; 362/32; 382/8; 358/106
[58] Field of Search ............. 358/101, 93, 106, 107; 362/32; 382/8; 350/96.24

[56] References Cited

U.S. PATENT DOCUMENTS

| | | | |
|---|---|---|---|
| 3,278,739 | 10/1966 | Royka | 362/32 |
| 4,269,515 | 5/1981 | Altman | 356/394 |
| 4,343,553 | 8/1982 | Nakagawa | 250/560 |
| 4,389,698 | 6/1983 | Cibie | 362/32 |
| 4,459,643 | 7/1984 | Mori | 362/32 |
| 4,530,036 | 7/1985 | Conti | 362/32 |
| 4,604,648 | 8/1986 | Kley | 358/101 |

Primary Examiner—Howard W. Britton
Attorney, Agent, or Firm—Burns, Doane, Swecker & Mathis

[57] ABSTRACT

A soldering inspection system wherein light is irradiated on a soldered part at different incident angles by a light emitting means to collect information indicative of three-dimensional configuration of the soldered part and discriminate whether or not the configuration is acceptable. The three-dimensional configurational information can be obtained with light irradiated at least from two positions mutually of different angles with respect to the soldered part, the inspection is thereby made from quantitative viewpoint, and a highly precise result of the inspection is obtainable.

16 Claims, 18 Drawing Figures

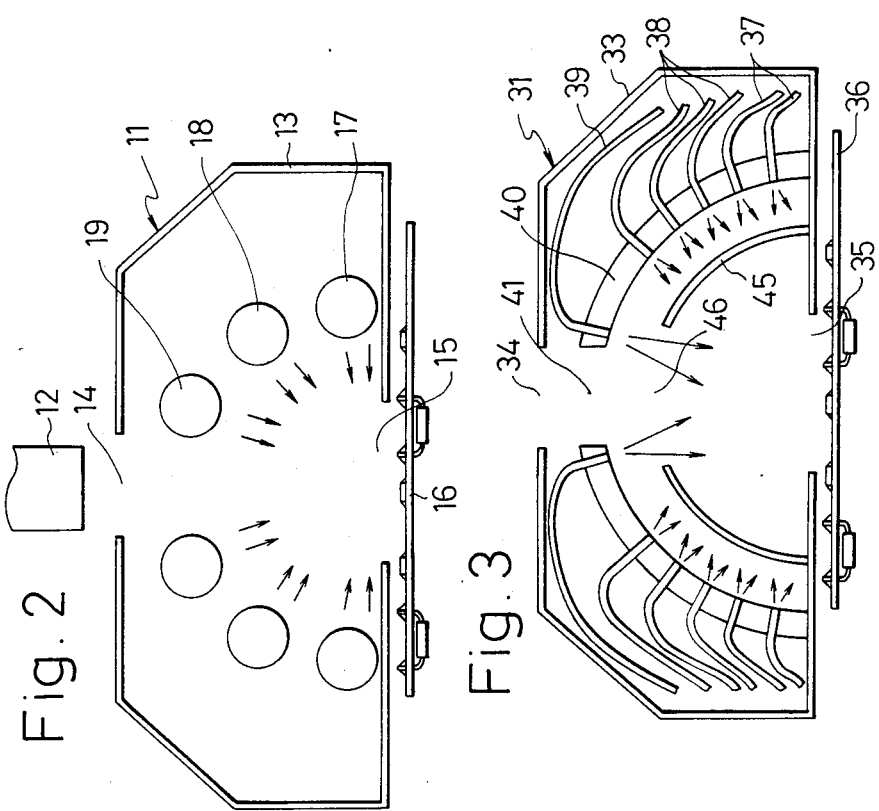
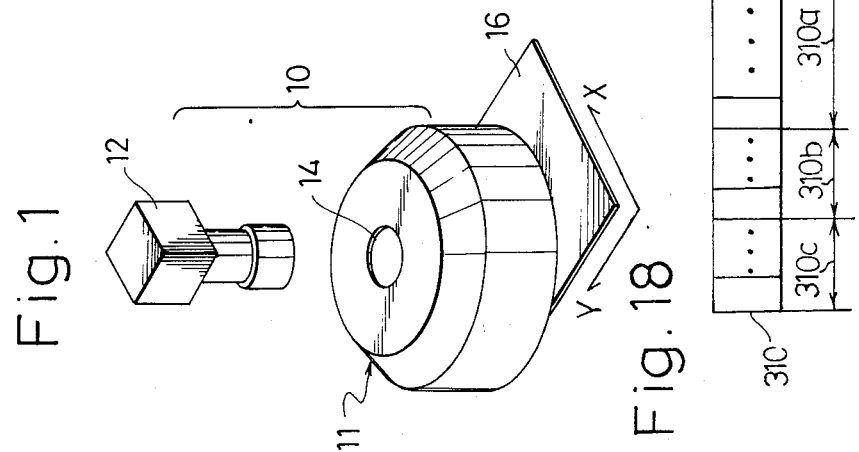

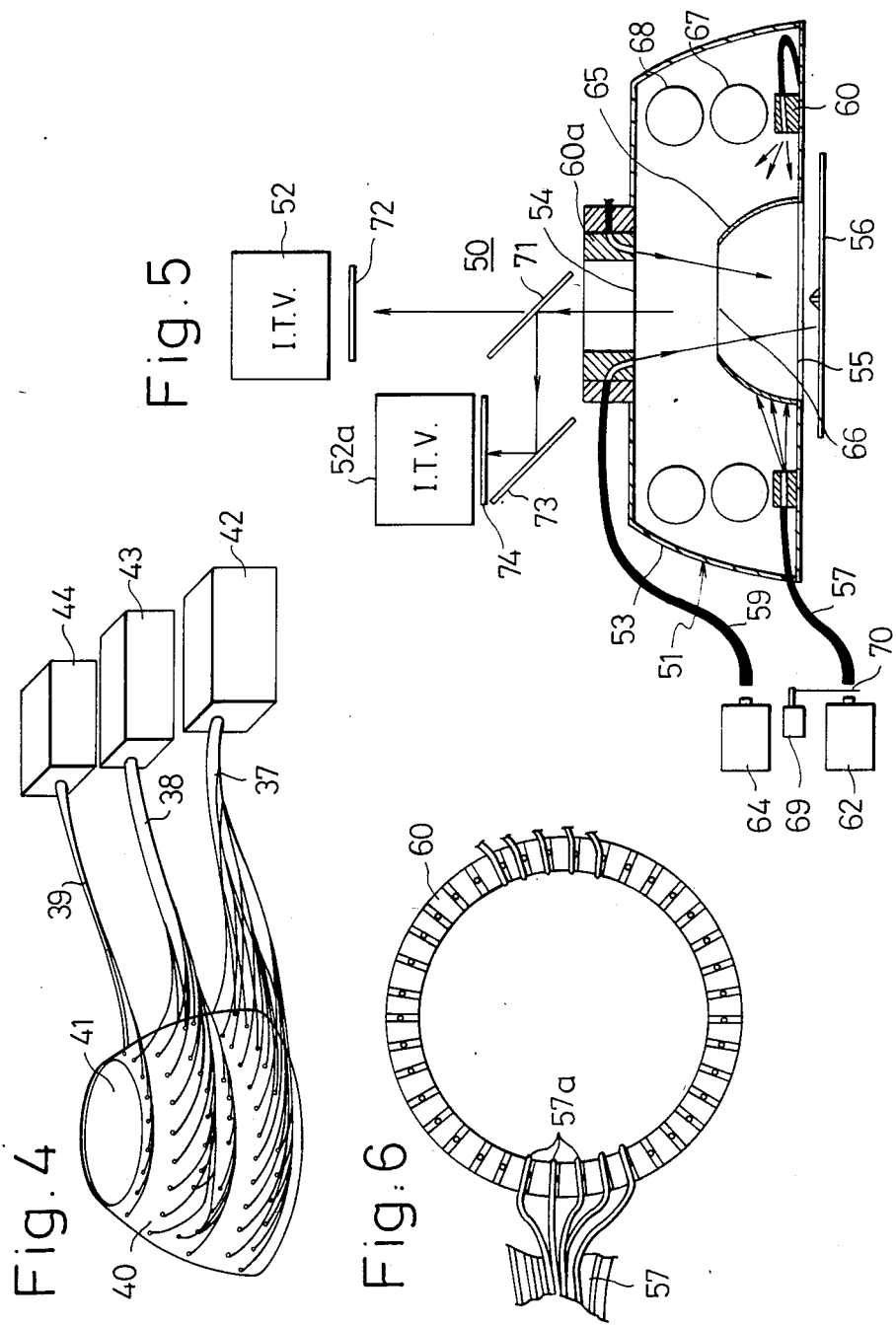

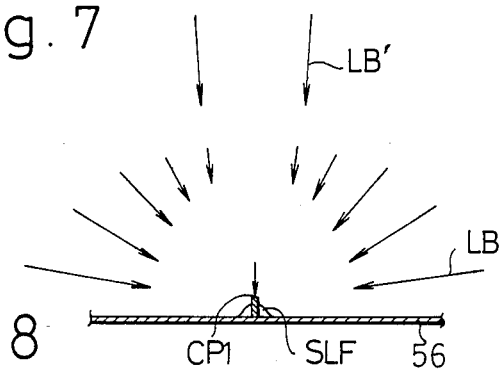
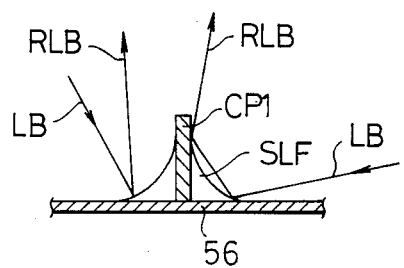
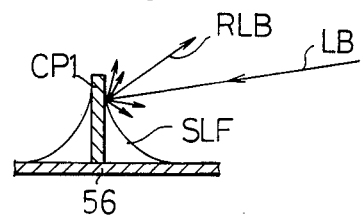
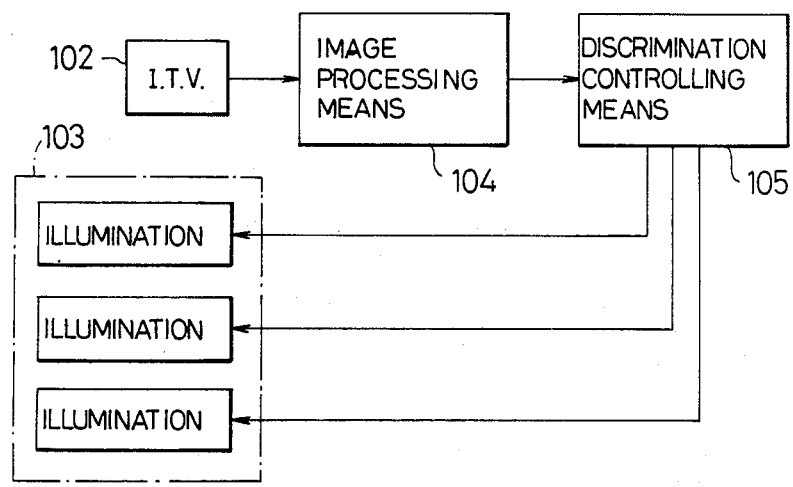

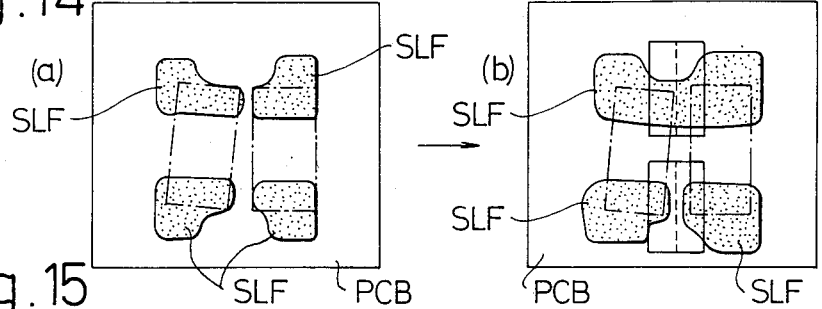
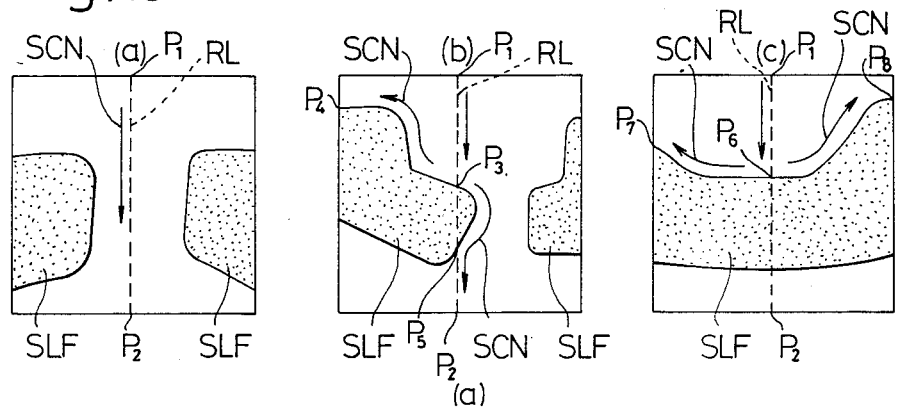
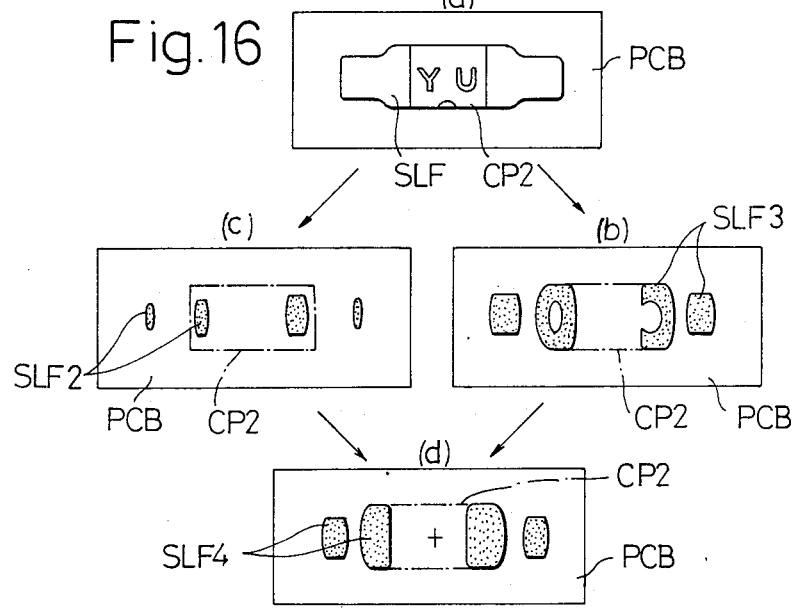

SOLDERING INSPECTION SYSTEM AND METHOD THEREFOR

TECHNICAL BACKGROUND OF THE INVENTION

This invention relates to soldering inspection systems and methods therefor and, more specifically, to a system and method for three-dimensionally inspecting soldered state of such electronic parts as circuit components carrying lead-wires, componental chips and the like which are soldered to a printed circuit board.

The soldering inspection system of the kind referred to is useful when operatively associated with an automatic soldering device or the like to automatically inspect any unfavorable mounting of the chips involving positional deviation and the like as well as any unfavorable soldering involving excessive or insufficient soldering with respect to a printed circuit board to which the lead-wire-carrying or chip components are soldered on mass production basis.

DISCLOSURE OF PRIOR ART

Generally, the automatic soldering of the lead-wire-carrying or chip components onto the printed circuit board have been enabled to be performed with a considerably high precision because of remarkable improvements in recent soldering technique. With respect to microelectronic chip components, however, the soldering has had to be carried out in a very fine region and has not been always complete, and it has been made necessary to inspect whether or not the mounting or soldering is favorable. The unfavorable mounting should be the positional deviation, configurational deficit and the like of the chips, and the unfavorable soldering should include lack of solder at intended location, insufficient amount of solder, excessive amount of solder including a state in which adjacent ones of soldered parts are bridged to each other by the solder placed over a predetermined region, and so on. Because these unfavorable mounting and soldering have been inspected with eyes of workers, the inspection has been defective in requiring high degree of skill. Yet, such visual inspection has to drive the worker's eyes very hard enough for easily causing any unfavorable state to be overlooked or discriminational fluctuation to occur so as not to be well adapted to the soldering in mass-production line, and it has been a general demand that the soldering inspection is automated.

An inspection system capable of contributing to the automation of soldering inspection has been disclosed in U.S. Pat. No. 4,269,515 to Norman G. Altman, in which a transparent pattern board forming a so-called artwork having a predetermined electrically conductive pattern is positioned parallelly with a printed circuit board and a laser beam is directed to the both boards while scanning in X and Y directions to compare the electrically conductive pattern on the printed circuit board with the electrically conductive pattern of the artwork and to discriminate any defect in the conductive pattern on the printed circuit board. According to Altman, the presence or absence of the soldered parts may be automatically determined by comparing the soldered parts as a part of the conductive pattern with the artwork pattern. That is, it appears possible, with the inspection system of Altman, to inspect such remarkable one of the unfavorable soldering as the lack of solder or bridged solder but, as Altman is to merely compare planar patterns with each other, it is hardly possible to clearly grasp if the placed solder is sufficient, insufficient or excessive in the volume. However, unfavorable connection is caused to occur not only by, for example, the lack of solder but also by the insufficient amount of solder, and the suggested system has been defective in this respect for realizing accurate and reliable inspection of the soldered parts.

There has been also disclosed in Japanese Patent Appln. Laid-Open Publication No. 57-33304 of Y. Nakagawa et al a configuration inspecting device, in which a linear slit light is intermittently projected on an object to be inspected, and the slit light as intercepted by the surface of the object is received and converted to an electrical waveform signal for comparison with a reference signal and discrimination of any difference therefrom. This device of Nakagawa et al allows the outer configuration of soldered part on a printed circuit board to be readable to some extent, but it has been still defective in the lack of quickness in the inspection because scanned image is obtained basically from a single slit light, and in the incapability of precisely determining the sufficiency of solder at the soldered part.

TECHNICAL FIELD OF THE INVENTION

A primary object of the present invention is, therefore, to provide a soldering inspection system which can grasp three-dimensionally the chip components or soldered parts on the printed circuit board or the like, to inspect any positional deviation or configurational deficit of the chip component, sufficiency or presence of bridging of the placed solder and the like with a high precision and quickness, and is well adapted to the mass-production soldering line.

According to the present invention, this object is realized by providing a soldering inspection system wherein light is irradiated from a light emitting means onto soldered parts with respect to electronic components, and information indicative of a surfatial configuration of the soldered part is detected for discriminating whether or not the soldered part is acceptable, the light emitting means being provided to cause emitted rays of light to be incident on the soldered part at different angles.

With such an arrangement, the irradiated light is incident on the soldered part at least from two positions to be at different angles, so that the present invention can obtain cubic or three-dimensional information dependent on surfatial configuration of the soldered part and discriminate whether or not the soldered part is acceptable in quantitative viewpoint for inspecting the sufficiency of placed solder highly precisely.

Other objects and advantages of the present invention shall become clear from the following description of the invention detailed with reference to preferred embodiments shown in accompanying drawings.

BRIEF EXPLANATION OF THE DRAWINGS

FIG. 1 is a schematic prespective view of an embodiment of a soldering inspection system according to the present invention, which including means for illuminating a soldered part and an industrial TV camera for monitoring the illuminated soldered part;

FIG. 2 is a schematic sectional view for showing the interior arrangement in one aspect of the system of FIG. 1, wherein lamps are used as the light emitting means;

FIG. 3 is a schematic sectional view for showing the interior arrangement in another aspect of the system of FIG. 1, wherein optical fibers are used as the light emitting means;

FIG. 4 is a schematic perspective view showing connecting relationship between the light emitting means employed in FIG. 3 and their associated light sources;

FIG. 5 is a schematic block diagram for showing another embodiment of the present invention, with its interior arrangement of the light emitting means;

FIG. 6 is a cross-sectional view at one of optical fiber holders of the light emitting means in the system of FIG. 5;

FIG. 7 is a diagram showing light distribution by means of the light emitting means in the embodiment of FIG. 5;

FIGS. 8 and 9 are diagrams showing respectively a state in which the irradiated light diffuses differently as irradiated from the emitting means of FIG. 5 and reflected on the soldered part;

FIG. 10 is a block diagram of a processing circuit for inspectional information used in an inspection method executed by the respective systems according to the present invention;

FIGS. 14 and 15 show diagrams for explaining respectively a specific example of the method according to the present invention;

FIG. 16 shows diagrams for explaining another specific example of the method according to the present invention;

FIG. 18 is a diagram showing conditional data for an image processing by means of the circuit shown in FIG. 17.

Figure 11:
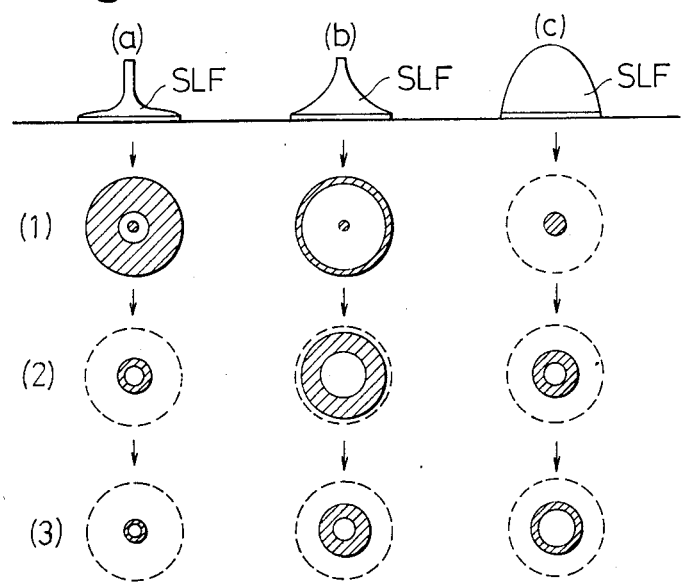
FIGS. 11 and 12 are diagrams for explaining respectively a manner in which the inspectional information obtained by the respective systems is discriminated according to the present invention.

While the present invention shall now be described with reference to the preferred embodiments shown in the drawings, it should be understood that the intention is not to limit the invention only to the particular embodiments shown but rather to cover all alterations, modifications and equivalent arrangements possible within the scope of appended claims.

DISCLOSURE OF PREFERRED EMBODIMENTS

According to one aspect of features of the present invention, there is provided a soldering inspection system which includes an illuminator arranged to illuminate a soldered surface from two or more positions of mutually different angles with respect to the surface. Referring to FIGS. 1 and 2, the soldering inspection system 10 generally comprises an illuminator 11 and an industrial TV camera 12, the illuminator 11 having a housing 13 which is provided in the center of top wall with an image pickup opening 14 and in the center of bottom wall with an illumination opening 15. Right above the pickup opening 14, the industrial TV camera 12 is fixed to a suitable mounting frame (not shown) and, right below the illumination opening 15, a printed circuit board 16 is placed on an X-Y table (not shown) performing X-Y indexing operations so that a target soldered part for the inspection in the printed circuit on the board will be positioned in the center of the illumination opening 15. Within the housing 13, circular lamps 17 to 19 of different diameters are provided at a plurality of stages (three stages in the illustrated embodiment) and are held by a proper supporting means (not shown), with the gradually less diametered circular lamps 17 to 19 disposed sequentially from the lowest stage to the highest stage, so as to form mutually different angles with respect to the target soldered part of the printed circuit board 16 disposed parallel to the bottom surface of the housing 13, and to thus realize different angled light irradiations onto the target soldered part of the printed circuit through the illumination opening 15. In the present instance, the lowermost lamp 17 of the relatively larger diameter can illuminate the target soldered part at an angle close to zero, while the uppermost lamp 19 of the relatively smaller diameter can illuminate the target at an angle close to 90 degrees. During each illumination by means of the respective lamps 17 to 19, the camera 12 can monitor the soldered surface including the inspection target through the pickup opening 14, axial spaces of the lamps 17 to 19 and illumination opening 15.

With such an arrangement, the illumination by these lamps 17 to 19 subjected to, for example, sequential lighting on and off will cause the illumination angle with respect to the target to be sequentially varied, whereby different images of the same inspection target respectively involving different emphasis depending on each of the different positional angles of the lamps 17 to 19 can be monitored through the camera. Because these images provide three-dimensional features in contrast to any flat or plannar image conventionally obtainable, a synthetic discrimination as to the acceptability of the soldered part as the inspection target is made possible from these monitored images, in such manner as will be made clear in a method of performing the inspection explained later.

According to the present invention, the lamps in the illuminator of the soldering inspection system may be replaced by optical fibers. Referring to FIGS. 3 and 4, a dome-shaped fiber holder 40 is disposed within a housing 33 of an illuminator 31 and provided in its top wall with an opening 41 of the same diameter as an image pickup opening 34 provided in the center of the top wall of the housing 33, which openings 34 and 41 being axially aligned with an illumination opening 35 made in the center of the bottom wall of the housing 33. The fiber holder 40 holds light emitting ends of optical fibers, dividing them into a plurality of groups 37 to 39 (three groups in the illustrated embodiment), the light emitting ends of the respective optical fiber groups 37 to 39 are fixedly passed through the holder 40 to open along a circular line or lines parallel to the bottom wall of the housing on the inner periphery of the holder 40, and the other ends of the respective groups are optically connected to each of light sources 42 to 43 which can be actuated independently of each other, so that the illumination can be provided to the inspection target in a printed circuit board 36 at different angles. In the present embodiment, the lowermost line group 37 can illuminate the target on the printed circuit board 36 at an angle close to zero, while the uppermost line group 39 can illuminate at an angle close to 90 degrees. Further, a smaller dome-shaped light diffuser 45 having a top opening 46 is disposed inside the holder 40 in coaxial relation therewith to diffuse only light emitted from the line groups 37 and 38. That is, the top opening 46 of the diffuser 45 is made to be larger in diameter than the opening 41 of the holder 40, so that light emitted from the uppermost optical fiber line group 39 will pass through the opening to illuminate directly the target disposed in the illumination opening 35 in the bottom of the housing 33.

With this arrangement, the total switching-over illumination time by means of the optical fiber line groups 37 to 39 can be made shorter than that in the embodiment of FIGS. 1 and 2, and required total inspection time can be speeded up. Other arrangement and operation are substantially the same as those of the foregoing embodiment of FIGS. 1 and 2, and members substantially equivalent to those of the foregoing embodiment are denoted by the same reference numerals but added by 20.

There is shown in FIGS. 5 and 6 a soldering inspection system 50 according to still another embodiment, which generally comprises an illuminator 51 and two industrial TV cameras 52 and 52a. The illuminator 51 comprises a housing 53 having axially aligned top and bottom openings 54 and 55, and first and second optical fiber holders 60 and 60a respectively of relatively larger and smaller diametered ring shape, the larger first holder 60 being provided on the bottom wall of the housing to enclose the bottom opening 55 within the housing while the smaller second holder 60a is secured to the periphery of the top opening 54. Circular fluorescent lamps 67 and 68 of a high-frequency lighted type are held within the housing by a proper supporting means over the first fiber holder 60, and a dome-shaped diffuser 65 having a central opening 66 is mounted on the peripheral part of the bottom opening 55 to have the opening 66 aligned with the top and bottom openings 54 and 55 within the housing 53. A first group of optical fiber lines 57 are held at their light emitting ends 57a by the first holder 60 so as to horizontally surround the diffuser 65, whereas a second group of optical fiber lines 59 are held at their light emitting ends in the second holder 60a so as to directly illuminate the inspection target on a printed circuit board 56 throught the opening 66 of the diffuser 65 and the bottom opening 55. In this case, the first group of the optical fiber lines 57 provide an illumination to the target on the board at an angle substantially parallel thereto, while the second group of the optical fiber lines 59 provided an illumination to the target at an angle close to 90 degrees thereto.

Between the other ends of the respective first and second groups of the optical fiber lines 57 and 59 and respective light-emitting ends of a pair of light sources 62 and 64 optically associated with the ends, a rotary shutter 70 of a shutter device 69 is provided so as to alternately intercept the emitted light from the both light sources 62 and 64 to the both groups 57 and 59. A half mirror 71 is disposed over the top opening 54 of the housing 53 so that reflected light from the solder surface of the target and reached the half mirror 71 will partly pass through the mirror and enter the TV camera 52 through a blue filter 72 and the remainder will be reflected by the mirror 71 and further by a reflection mirror 73 to enter the other TV camera 52a through a red filter 74.

With such arrangement, as the alternate shutter device 69 is operated, the target solder surface is subjected to an alternate illumination of diffused light beams LB with horizontal light of the first group fibers 57 and lamps 67 and 68 emphasized and vertically-falling light beams LB' with vertical light of the second group fibers 59 emphasized, as shown in FIG. 7. Referring to FIGS. 8 and 9, the diffused light beams LB of the illuminator 51 cause variously angled light beams to be incident on soldered face SLF of a lead-wire-carrying CP1 or chip component CP2 incorporated into the printed circuit board 56, in which vertically upward reflected light amount is remarkably decreased at a region where the angle of inclination of the soldered face SLF exceeds 45 degrees. It is preferable, therefore, to increase the horizontally incident light amount for increasing the vertically reflected light beams at the region exceeding the 45 degrees, and the present embodiment of FIGS. 5 and 6 effectively makes it possible to optimumly set a ratio between the horizontally incident and vertically incident light beam intensities to be in a range of 10:1 to 10:5.

Such spectrographic image monitoring as achieved by means of the half mirror 71 for the reflected light beams received through the top opening 54 and further through such different color filters as blue and red filters renders simultaneous monitoring of the image in different colors to be possible, which is particularly effective when it is desired to simultaneously discriminate, for example, a region of insufficient solder and another region lacking the solder and exposing copper or the like conductor face.

According to another feature of the present invention, there is provided a method in which the soldering inspection systems of the respective embodiments referred to above are used to inspect the soldered part three-dimensionally on the basis of the images obtained through the industrial TV system including the camera. Referring to FIG. 10, an image monitored by the camera of the soldering inspection system is sent from an industrial TV 102 to an image processing means 104 where an operation for obtaining respective area values of, for example, white and black regions in the image is performed and operational result is supplied to a discrimination controlling means 105 which discriminates whether or not the soldered part is acceptable according to a proper discrimination algorithm. In the present instance, further, the discrimination control means 105 is designed to discriminate an image obtained with the illumination at a certain angle, and to thereafter switch over the light sources of an illuminator 103 so as to provide another image obtained with the illumination at another angle, and the means 105 preferably includes a sequence program which performs actuation of the X-Y table for indexing the soldered parts of the printed circuit board in a predetermined sequence along the X-Y axes.

A practical discrimination procedure will be described with reference to FIGS. 11 and 12, in which FIG. 11 shows examples of images of three different states of the soldered part SLF with respect to a lead wire, in which (a) is of insufficient state, (b) is of a proper state, and (c) is of excessive state. In discriminating these states, the three-stage illumination sources in the inspection systems of FIGS. 1 and 2 or FIGS. 3 and 4 are energized sequentially from the topmost one to the lowermost. In the drawing, images (1) are of the illumination source close to the 90 degree position, images (2) are of the source close to 45 degree position, and images (3) are of the source close to horizontal, wherein hatched zone denotes bright white part in the image. It will be appreciated from these images that the white part becomes excessively large in the insufficiently soldered state particularly upon the close-to-90 degrees illumination but becomes remarkably small in the excessively soldered state upon all other angled illuminations so that the discrimination between the both states can be easily made.

Figure 12:
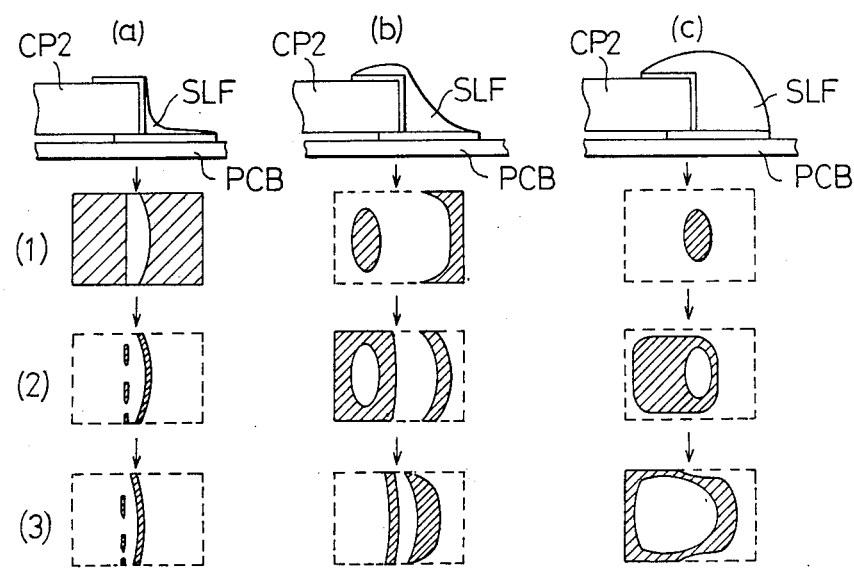

FIG. 12 shows examples of images also of different states of the soldered part SLF for connecting the chip component CP2 to the printed circuit board PCB, in which (a), (b) and (c) also show the insufficient, proper and excessive soldered states, respectively, and the illumination is performed in the same manner as in the case of FIG. 11. It will be understood from FIG. 12 that the arrangement for illuminating the soldered part of the chip component sequentially at different angles makes it possible to easily and reliably discriminate the respective soldered states from each other.

Figure 13:
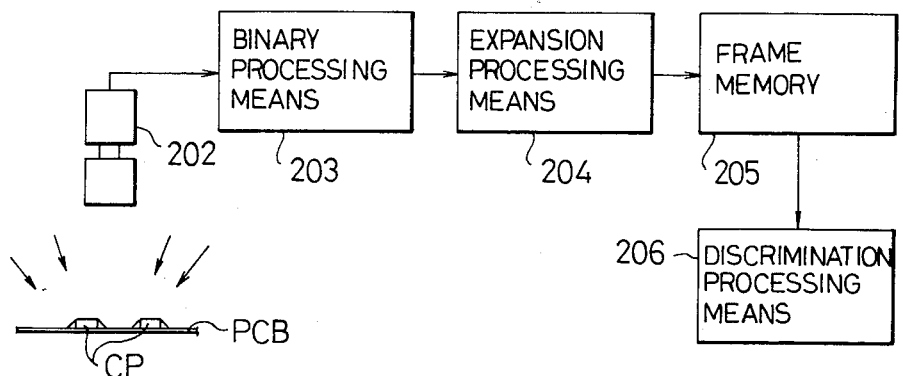
FIG. 13 is a block diagram of an inspectional information processing circuit used in another method according to the present invention.

In FIG. 13, there is shown another example of the soldering inspection method, in which the soldered part is monitored by an industrial TV camera 202 as an image in which the soldered part appears white, and the image is sent from the camera 202 to a binary processing means 203 in the soldering inspection system. In this means 203, a threshold value for the white zone corresponding to the soldered part is set to perform the binary processing so as to present any other region than the soldered part in black. The means 203 also performs a noise processing and sends such an image output as shown in FIG. 14(a) (in which the white zone is denoted by dotted zone) to an expansion processing means 204, in which the white zones of the binary processed image of the soldered parts are expanded to render the limit proximity distance between adjacent ones of soldered parts to be ½, as shown in FIG. 14(b). This expanded output of the means 204 is once stored in a frame memory 205 and later sent to a discrimination processing means 206 to discriminate the bridged state or excessively close state between the adjacently disposed soldered parts.

In the discrimination processing means 205, such a discrimination sequence, preferably, as shown in FIGS. 15(a) to (c) is executed, in which drawings rectangular parts defined by a solid line in FIG. 14(b) are shown as magnified. Here, a scanning SCN is carried out between both vertically extreme points $P_1$ and $P_2$ of a reference line RL so that, when the scanning does not hit any soldered part SLF as shown in FIG. 15(a), it is discriminated that the soldering is proper. If the scanning SCN hits one of the soldered parts at a point $P_3$ as shown in FIG. 15(b) in the normal scanning direction from the point $P_1$ to the point $P_2$, then the scanning direction is changed to another and, when the scanning in the another direction reaches a point $P_4$ at a side edge of the frame as shown in FIG. 15(b), the scanning is continued again from the point $P_3$ in still another direction. When this continued scanning reaches the reference line RL at a point $P_5$, the scanning goes on along the reference line RL until the point $P_2$ is reached, and it is judged that the soldered part is proper. When the scanning SCN hits a bridging part of the soldered part SLF at a point $P_6$ as shown in FIG. 15(c) during the normal scanning from the point $P_1$ toward the point $P_2$, the scanning direction is changed but, if the direction-changed scannings reach only both side edge points $P_7$ and $P_8$ and cannot go on along the line RL over the point $P_6$, the discrimination is made in such that the bridging is present and the soldering is faulty.

According to the present example, the magnified image processing of the soldered parts with ½ representation of their limit proximity distance renders the discrimination not only of the bridged state between the adjacent soldered parts but also of the excessively close state therebetween to be easily and reliably performed.

There is shown in FIG. 16 a further example of the soldering inspection method, in which the foregoing horizontally-emphasized diffusion illumination is directed onto such soldered parts SLF as shown in FIG. 16(a) which connecting a chip component CP2 to the printed circuit board PCB, thereby monitored image signal is subjected to the binary processing at an optimum level so as to trim off images of the chip component CP2 as well as any characters thereon, and such an image of soldered parts SLF3 as shown in FIG. 16(b) is obtained, which is then stored in a suitable memory. Next, the foregoing vertically-falling illumination close to the 90 degrees is provided to the same soldered chip components CP2, the image signal of which is also processed to be optimumly binary coded for trimming off images of the chip component CP2 and any characters thereon, and such an image of the soldered parts SLF2 as shown in FIG. 16(c) is obtained. Both of the images of FIGS. 16(b) and (c) are combined to form such a composite image of soldered parts SLF4 as shown in FIG. 16(d), this composite image is compared with a predetermined reference image, and the discrimination of the state of the soldered parts can be carried out with a high precision.

Figure 17:
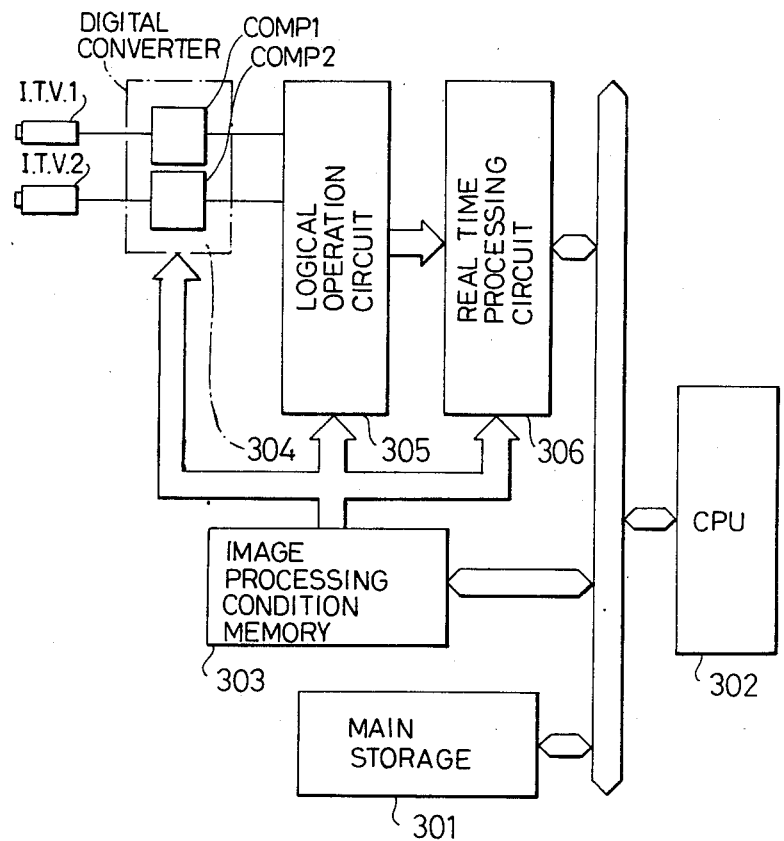
FIG. 17 is a block diagram of an inspectional information processing circuit used in still another method according to the present invention.

Shown further in FIG. 17 is a still another example of the soldering inspection method which is more practical than that of FIG. 10. In the present instance, there are used a main storage device 301 storing conditional information for processing images monitored, for example, by two industrial TV cameras 1 and 2, and a CPU 302 for fetching at a high speed the stored information out of the main storage. Here, the conditional information is a set of image-processing conditional data respectively corresponding to each of picture elements for the monitored image, and as shown in FIG. 18 the image-processing conditional data 310 comprise a plurality of bits corresponding to the picture elements and including, for example, inspection-area-specifying number bits 310a, logical-operation mode bits 310b and switch-over bits 310c. Responsive to a predetermined command, the CPU 302 provides an image-processing conditional information output to an image processing condition memory 303 which in turn applies an output to a digital converter 304, a logical operation circuit 305 and a real-time processing circuit 306 and a conditional command is provided to the respective circuits. On the other hand, the images monitored by the cameras 1 and 2 are applied respectively to each of comparators COMP1 and COMP2 in a digital converter 304, where the images are converted to the two or more valued outputs in response to a discrimination level received from the condition memory 303, and these outputs are provided to the logical operation circuit 305. In this circuit 305, an operation is carried out in response to the image-processing conditional data from the condition memory 303 and a resultant output is provided to the real-time processing circuit 306 where an operation for obtaining the area and the like is carried out for each predetermined zone of the soldered part in response to the data from the condition memory 303. In this arrangement, the circuits 304, 305 and 306 are operated in synchronism with the scanning of the industrial TV cameras, and a real time discrimination of the state of the entire soldered parts can be realized at a high speed.

What is claimed as our invention is:

1. A soldering inspection system wherein light is emitted from a plurality of light-emitting means onto soldered parts which are disposed with respect to electronic components on an object such as a printed circuit board or the like, and information indicative of a multi-dimensional surficial configuration of said soldered parts is detected for determining the acceptability of the soldered parts, said plurality of light-emitting means being arranged to produce emitted rays of light incident on each soldered part from different angles relative to a plane of said object, including a substantially zero degree angle, a substantially 90 degree angle, and at least one intermediate angle therebetween, means for sequentially actuating said plurality of light-emitting means to emit light sequentially from said different angles, and detecting means for detecting the object while the object is illuminated sequentially from said different angles for producing a plurality of signals representative of a multi-dimensional configuration of the surface of each soldered part.

2. A system according to claim 1, wherein said detecting means includes an industrial TV camera oriented at a 90 degree angle relative to a plane of said object.

3. A system according to claim 1, wherein said light emitting means comprises a horizontally-emphasized diffusion illumination source with increased horizontally irradiated light beams, and a vertically-falling illumination source with irradiated light beams at an angle close to 90 degrees with respect to the plane of said soldered parts.

4. A system according to claim 3, wherein said illumination sources respectively comprise optical fiber lines optically connected to a light source arranged for alternate lighting on and off.

5. A system according to claim 3, wherein said illumination sources respectively comprise a circular lamp.

6. A system according to claim 3, wherein said illumination sources are disposed in a housing, and said light emitting means forming the respective illumination sources comprises a group of optical fiber lines optically connected at one end to each of alternately actuated light sources and held at the other end by a holder provided to said housing.

7. A system according to claim 6, wherein said housing is provided in a top wall thereof with an image pickup opening and in a bottom wall thereof within an illumination opening for disposing therebelow said soldered parts to be illuminated by said illumination sources, said detecting means comprising an industrial TV camera disposed above sad image pickup opening.

8. A system according to claim 6, wherein said holder for said optical fiber lines is dome-shaped and disposed within said housing.

9. A system according to claim 6, wherein said holder for said optical fiber lines comprises a first ring-shaped member secured to the bottom wall of said housing to hold the lines for said diffusion illumination source, and a second ring-shaped member secured on the periphery of said image pickup opening of the housing to hold the lines for said vetically-falling illumination source.

10. A system according to claim 8, wherein said light emitting means further comprises a fluorescent lamp of high-frequency type and disposed above said first ring-shaped holder member.

11. A soldering detection method for determining the acceptability of soldered parts disposed with respect to electronic components on an object such as a printed circuit board or the like, said method comprising the steps of actuating a plurality of light-emitting means for directing a plurality of beams of light toward said soldered parts such that said light beams are incident on each soldered part from different angles relative to a plane of said object, including a substantially zero degree angle, a substantially 90 degree angle, and at least one intermediate angle therebetween, actuating said plurality of light means sequentially to emit light sequentially from said different angles, and detecting the object while the object is illuminated sequentially from different angles for producing a plurality of signals representative of a multi-dimensional configuration of the surface of each soldered part.

12. A method according to claim 11, wherein said plurality of signals is transformed into a plurality of images of said soldered parts.

13. A method according to claim 12, wherein said plurality of images are obtained on real time basis, and a real time operation is performed with respect to each picture element of the respective images in response to a predetermined image-processing conditional information of said discrimination.

14. A method according to claim 12, wherein said plurality of images are respectively binary valued for said discrimination.

15. A method according to claim 14, wherein said binary valued images are expanded by a magnification predetermined with respect to the limit proximity distance between adjacent ones of said soldered parts for said discrimination.

16. A method according to claim 14, wherein said binary valued images are combined into a composite image for said discrimination.

* * * * *